United States Patent [19]

Deguchi et al.

[11] 4,205,990
[45] Jun. 3, 1980

[54] PROCESS FOR FORMING A CYAN DYE IMAGE BY THE USE OF A 2-EQUIVALENT CYAN COUPLER

[75] Inventors: Hidetaka Deguchi; Takaya Endo; Shoji Kikuchi; Toshiki Komaita, all of Hino, Japan

[73] Assignee: Konishiroku Photo Industry Co., Ltd., Nihonbashi-Muro, Japan

[21] Appl. No.: 948,651

[22] Filed: Oct. 3, 1978

Related U.S. Application Data

[63] Continuation of Ser. No. 710,244, Jul. 30, 1976, abandoned.

[30] Foreign Application Priority Data

Aug. 2, 1975 [JP] Japan .................................. 50-94294

[51] Int. Cl.² .......................... G03C 7/00; G03C 1/40
[52] U.S. Cl. .................................. 430/380; 430/472
[58] Field of Search ........................ 96/55, 100 R, 74

[56] References Cited

U.S. PATENT DOCUMENTS

| | | | |
|---|---|---|---|
| 3,551,157 | 12/1970 | Salminen | 96/100 |
| 3,620,747 | 11/1971 | Marchant et al. | 96/100 |
| 3,632,373 | 1/1972 | O'Connell et al. | 96/100 |
| 4,012,258 | 3/1977 | Kojima et al. | 96/100 |
| 4,052,212 | 10/1977 | Deguchi et al. | 96/100 |

*Primary Examiner*—Travis J. Brown
*Attorney, Agent, or Firm*—Haseltine, Lake & Waters

[57] ABSTRACT

A process for forming a cyan dye image by using a novel photographic 2-equivalent cyan coupler which is characterized by having a splitt-off group of the below-indicated general formula at the active position of the cyan coupler so that the oxy portion is present on the side of the active position:

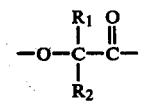

wherein $R_1$ and $R_2$ stand for a hydrogen atom or an organic group, provided at least one of $R_1$ and $R_2$ should be an organic group, is disclosed.

8 Claims, No Drawings

PROCESS FOR FORMING A CYAN DYE IMAGE BY THE USE OF A 2-EQUIVALENT CYAN COUPLER

This is a Rule 60 continuation of U.S. Patent Application Ser. Number 710,244, filed July 30, 1976, now abandoned.

The present invention relates to a novel coupler for use in photography. More particularly, the invention relates to a novel cyan coupler employed in photography using silver halides as photosensitive components.

In photography, a silver halide is broadly used as a photosensitive component for recording light information because it is excellent in photographic properties such as the sensitivity and gradation. When a silver halide is used as a photosensitive component and it is intended to obtain a color image, the silver halide generally is combined with a certain kind of a color-forming compound, and in response to the information recorded by the silver halide, this color-forming compound is reacted with a certain kind of a reactive compound to form a dye, i.e., a dye image. This color-forming compound is a so-called coupler and in general, the reactive compound to be used in combination with the coupler for forming of a dye is a color developer, for example, a developer of the aromatic primary amine type.

As is well known in the art, when light information is recorded and a silver halide having a development nucleus is developed in the presence of a coupler with a color developer, the color developer reduces the silver halide to developed silver and the color developer per se is oxidized. Accordingly, an active oxidation product of the color developer is formed and it reacts with the coupler to form a dye and a dye image corresponding to the information recorded on the silver halide.

The reaction between the coupler and the color developer is caused to occur at the active position of the coupler, and in general, the active position is present on an active methine or methylene group in the coupler molecule.

A coupler having a hydrogen atom at this active position is called a 4-equivalent coupler, and a coupler having at this active position a so-called split-off group which can readily split off during the reaction of the coupler with the color developer is called a 2-equivalent coupler.

When the 4-equivalent coupler reacts with the color developer, it requires four equivalents of the silver halide having a development nucleus per active position, but the 2-equivalent coupler requires only two equivalents of the silver halide per active position. Accordingly, in general, the 2-equivalent coupler provides a dye image of a higher concentration when the amount of the developed silver is the same. In case of the 2-equivalent coupler, if a group (linking group) at the joint portion of the split-off group linked to the active position is appropriately chosen it is possible to impart a development-inhibiting activity to a compound by splitting-off of the split-off group. For example, a 2-equivalent coupler having a split-off group including a thio (—S—) group as the linking group is called a development inhibitor releasing coupler (DIR coupler). Since in this coupler the development is inhibited in proportion to the quantity of the developed silver, this coupler can be used for various applications. For example, the DIR coupler exhibits so-called intraimage effects such as the effects of controlling the image tone and making the image particles finer in the layer into which the coupler has been incorporated and inter-image effects such as the effect of improving the color hue in other layers. Further, by utilizing the actions of the DIR coupler to other layers, it is used for the diffusion transfer system.

Moreover, some 2-equivalent couplers, for example, those having a dye portion in the split-off group, can be used for the diffusion transfer system by utilizing the split dye for formation of a color image of the diffusible dye on an image-receiving layer. The coupler of this type is called a diffusible dye releasing coupler (DDR coupler). Furthermore, some colored 2-equivalent couplers have an masking effect of complementing a dye image. A coupler of this type is called a colored coupler.

As will be apparent from the foregoing illustration, 2-equivalent couplers are substantially excellent over 4-equivalent couplers and they are broadly used because of their various applicabilities.

Although known 2-equivalent couplers are superior to 4-equivalent couplers in various properties, they are still insufficient in some points. For example, the dye-forming speed is low and 2-equivalent couplers tend to impart fog to a silver halide-containing photosensitive layer or stain the photosensitive layer. Still further, they cannot be dispersed into photosensitive layers at sufficient concentrations. Accordingly, it has been desired to improve 2-equivalent couplers in these insufficient points.

It is therefore a primary object of the present invention to provide a novel 2-equivalent coupler in which the foregoing defects involved in conventional products can be overcome.

Another object of the present invention is to provide a 2-equivalent cyan coupler excellent in photographic characteristics.

Still another object of the present invention is to provide a silver halide photosensitive material including such 2-equivalent cyan coupler or a photographic process using such 2-equivalent cyan coupler.

In accordance with the present invention, more specifically, there is provided a photographic 2-equivalent cyan coupler which has a split-off group including as the linking group a divalent group of the following general formula [I] on the active position of the cyan coupler so that the oxy portion is present on the side of the active position:

The 2-equivalent cyan coupler of the present invention has a high dye-forming speed because of the specific linking group and it does not impart fog or dye stain to a photosensitive layer. Further, it has a good dispersibility into the layers of a photographic sensitive material, such as a photosensitive layer, and therefore, it can be dispersed into these layers at high concentrations. A dye obtained from this cyan coupler has an excellent durability to light, heat and temperature and has such an excellent absorption characteristic that it has none of unnecessary absorptions but shows a sharp absorption. Still further, it is free of a development inhibiting property as possessed by some conventional 2-equivalent couplers.

For example, when the 2-equivalent cyan coupler of the present invention is incorporated into a silver halide photographic sensitive material, the thickness of the photosensitive layer can be remarkably reduced, and a high resolving power and a high sharpness in the dye image can be attained. Still further, in case of a multilayer photosensitive material, permeation of light into lower layers can be improved and the photographic sensitivity is therefore improved.

Typical 2-equivalent cyan coupler of the present invention are represented by the following general formulas [II] and [III]:

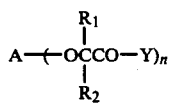

(II)

wherein $R_1$ and $R_2$ stand for a hydrogen atom or an organic group, provided at least one of $R_1$ and $R_2$ should be an organic group; A stands for an n-valent cyan coupler residue, Y stands for a monovalent or divalent organic group; and $R_1$ or $R_2$ may be bonded through the Y group to the carbon atom of the carbonyl group to form a ring, with the proviso that in this case $R_1$ or $R_2$ and Y stand for a divalent organic group, and

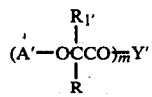

(III)

wherein $R_1'$ and $R_2'$ stand for a hydrogen atom or an organic group, provided at least one of $R_1'$ and $R_2'$ should be an organic group; A' stands for a monovalent cyan coupler residue; Y' stands for an organic group having a valence of 2 or higher, and $R_1'$ or $R_2'$ may be bonded through the Y' group to the carbon atom of the carbonyl group to form a ring, with the proviso that in this case $R_1'$ or $R_2'$ stands for a divalent organic group and Y' stands for an organic group having a valence of 3 or higher.

Types of the above general formulas [II] and [III] are typical instances of the coupler of the present invention, and a 2-equivalent coupler composed of a mixture of couplers of the formulas [II] and [III] is included in the scope of the present invention. In the above general formulas [II] and [III], the cyan coupler residue is a residue formed by removing the hydrogen atom or split-off group on the active position of the cyan coupler, and when a plurality of active positions are present in one molecule, split-off groups introduced into these active positions may be same or different or a hydrogen atom may be introduced to any of these active positions. In the present invention, however, it is preferred that the split-off groups of the present invention be introduced into all of the active positions.

In the above general formulas [II] and [III], as $R_1$, $R_2$, $R_1'$ and $R_2'$, there can be mentioned, for example, a hydrogen atom, a nitro group, a hydroxyl group, a cyano group, a carboxyl group, an amino group, a substituted amino group, a sulfo group, and substituted and unsubstituted alkyl, alkenyl, aryl, heterocyclic, alkoxy, aryloxy, arylthio, arylazo, acylamino, carbamoyl, ester, acyl, acyloxy, sulfonamido, sulfamoyl, sulfonyl, morpholino, piperazyl and imidazolyl groups. Further, divalent aliphatic hydrocarbon residues, aromatic hydrocarbon residues or heterocyclic residues and composite divalent groups comprising two or more linked groups selected from the above recited groups are included. Moreover, these groups may be substituted. $R_1$ and $R_2$ (or $R_1'$ and $R_2'$) may be bonded together to form a ring. In this case, $R_1$ and $R_2$ or $R_1'$ and $R_2'$ stand for a divalent organic group.

Preferred examples of the group Y in the general formula [II] include aliphatic hydrocarbon residues, aromatic hydrocarbon residues, heterocyclic residues, alkoxy groups, phenoxy groups, naphthoxy groups, aliphatic hydrocarbon amino residues, heterocyclic amino residues and mercapto groups, and these groups may be substituted. Preferred examples of the group Y' in the general formula [III] include m-valent aliphatic hydrocarbon residues, aromatic hydrocarbon residues, heterocyclic residues, alkylenedioxy groups, arylenedioxy groups, alkylene diamino residues, arylene diamino residues and heterocyclic diamino residues, and these groups may be substituted. Further, the group Y' may be an m-valent composite group including two or more linked groups selected from the foregoing groups, for example, a divalent group including a divalent aliphatic hydrocarbon residue and an arylene group bonded together. In this case, k (a positive number) of divalent aliphatic groups and l (a positive number) of arylene groups may be bonded in a block or random style. Further, these m-valent groups may have an oxygen atom, an imino group or the like at the terminal end thereof. Furthermore, two adjacent carbon atoms in the m-valent group may be interrupted by an oxygen atom, a sulfur atom, an imino group, a sulfonyl group, a carbonyloxy group, an aminocarbonyl group, a sulfoamido group or the like. In the above general formulas [II] and [III], n and m are preferably 1 or 2. However, in the case a cyan coupler known as a polymer coupler is used as the coupler base, n and m may be 3 or more.

As the cyan coupler residue of a preferred typical coupler that is used in the present invention, there can be mentioned, for example, those represented by the following general formulas [IV], [V] and [VI]:

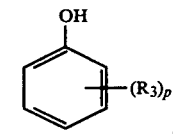

[IV]

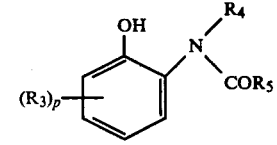

[V]

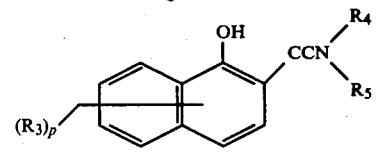

[VI]

In the foregoing general formulae, $R_3$ stands for a hydrogen atom, a halogen atom, an aliphatic hydrocarbon residue, an acylamino group or a group $-O-R_6$ or $-S-R_6$ (in which $R_6$ stands for an aliphatic hydrocarbon residue), and when two or more of $R_3$ groups are present in one molecule, they may be same or different. The aliphatic hydrocarbon residue may be substituted. $R_4$ and $R_5$ are groups selected from aliphatic hydrocarbon residues, aryl groups and heterocyclic residues. One of them may be a hydrogen atom, and these groups may be substituted. Moreover, $R_4$ and $R_5$ may be bonded together to form a nitrogen-containing hetero ring. p is an integer of 1 to 4 (in the general formula [V], p is an integer of 1 to 3), and q is an integer of 1 to 5. The aliphatic hydrocarbon residue may be saturated or unsaturated, or it may be linear, branched or cyclic. As preferred examples of the aliphatic hydrocarbon residue, there can be mentioned alkyl groups such as methyl, ethyl, isobutyl, dodecyl, octadecyl, cyclobutyl and cyclohexyl groups, and alkenyl groups such as an allyl group. Typical instances of the aryl group include phenyl and naphthyl groups. As the heterocyclic residue, there can be mentioned for example, pyridyl, quinolyl, thienyl, piperizyl and imidazolyl groups. As the substituent to be incorporated into such aliphatic hydrocarbon residue, aryl group or heterocyclic residue, there can be mentioned a halogen atom, a nitro group, a hydroxyl group, a carboxyl group, an amino group, a substituted amino group, a sulfo group, and substituted and unsubstituted alkyl, alkenyl, aryl, heterocyclic, alkoxy, aryloxy, arylthio, arylazo, acylamino, carbamoyl ester, acyl, acyloxy, sulfonamido, sulfamoyl, sulfonyl, morpholino, piperazyl and imidazolyl groups. The hetero ring formed by $R_4$ and $R_5$ is preferably a nitrogen-containing hetero ring selected from the above-mentioned heterocyclic residues.

In the above-mentioned general formulas [II] or [III], the aliphatic hydrocarbon residue may be saturated or unsaturated, or it may be linear, branched or cyclic. As typical instances of the monovalent aliphatic hydrocarbon residue, there can be mentioned alkyl and alkenyl groups, preferably methyl, ethyl, isobutyl, octyl, t-octyl, octadecyl, cyclobutyl, cyclohexyl and 2-norbonyl groups. As typical instances of the divalent aliphatic hydrocarbon residue, there can be mentioned alkylene groups, preferably methylene, ethylene, butylene and hexylene groups. As typical instances of the aromatic hydrocarbon residue, there can be mentioned aryl and arylene groups, preferably phenyl, naphthyl, phenylene and naphthylene groups. Preferred examples of the heterocyclic residue include 5- and 6-membered heterocyclic residues containing a hetero atom such as nitrogen, oxygen and sulfur. For example, there can be mentioned monovalent groups such as thienyl, pyridyl, quinolyl and oxadiazolyl groups and divalent groups such as pyridinylene and quinolylene groups. Acetyl, benzoyl and naphthoyl groups are preferred as the acyl group, and thioacetyl, thiobenzoyl and thionaphthoyl groups are preferred as the thioacyl group. As the sulfonyl group, there can be mentioned phenylsulfonyl, chlorosulfonyl and methanesulfonyl groups.

In the above general formulas [II] or [III], the groups Y and Y' may be substituted as mentioned above, and as the substituent, there can be mentioned those exemplified above with respect to the general formulas [IV], [V] and [VI].

Typical examples of the split-off group containing as the linking group a divalent group represented by the general formula [I] are as follows:

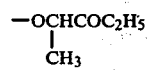

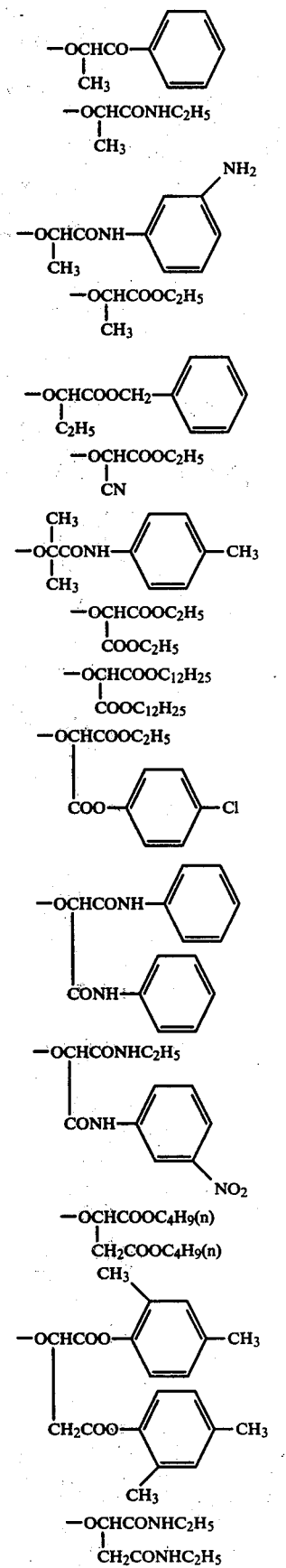

Couplers containing a split-off group such as mentioned above at the active position of the cyan coupler as indicated by the general formula [IV], [V] or [VI] are preferably employed in the present invention. The reason why the coupler of the present invention has the above-mentioned excellent photographic characteristics is considered to be that it has a specific linking group as mentioned above.

Typical examples of the coupler of the present invention are described below, though couplers that can be used in the present invention are not limited to these couplers.

-continued (6) 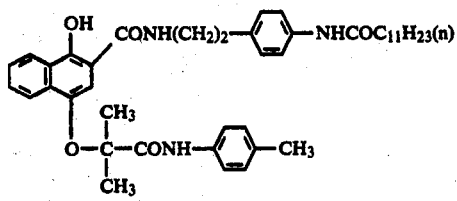

(7) 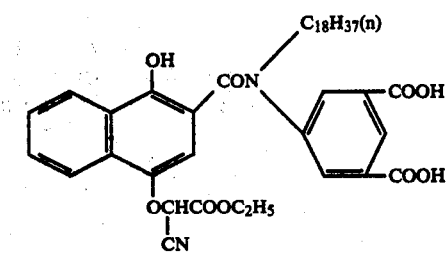

(8) 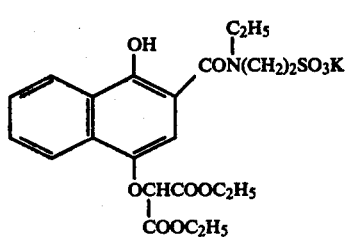

(9) 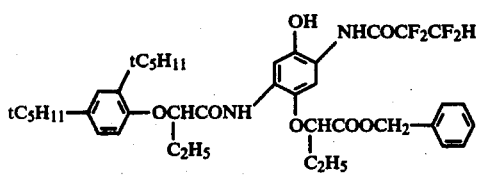

(10) 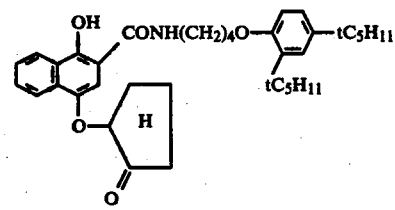

(11) 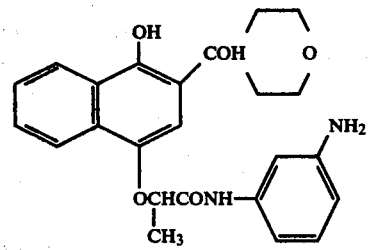

(12) 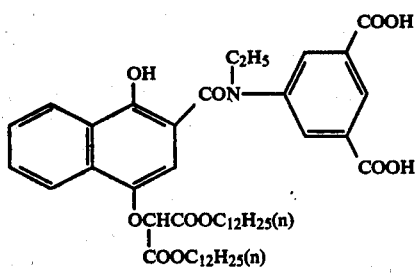

-continued

(13) 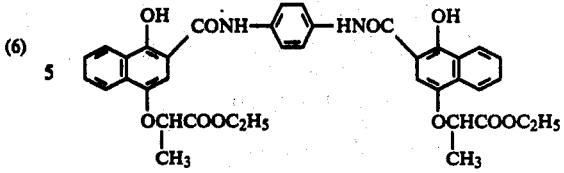

The foregoing compounds of the present invention are prepared according to the following methods.

For example, a coupler of the naphthol type can be synthesized according to the method disclosed in *Journal of the American Chemical Society*, 64, 798 (1942). More specifically, 1,4-dihydroxy-2-naphthoic acid is reacted with a carbonyl compound containing a halogen atom or other substituent at a corresponding α-chloro-α-alkyl acetate, α-bromo-α-alkyl acetylamide or α-bromo-α-alkoxycarbonylmethyl acetate in a solvent such as acetone, dimethyl formamide or the like in the presence of pyridine, sodium carbonate, sodium hydroxide or the like at room temperature or an elevated temperature, and the resulting naphthoic acid, for example, 1-hydroxy-4-(1-ethoxycarbonylethoxy)-2-naphthoic acid, 1-hydroxy-4-(1-ethylaminocarbonylethoxy)-2-naphthoic acid, 1-hydroxy-4-(diethylsuccinyloxy)-2-naphthoic acid or the like, is converted to the corresponding phenyl ester or acid chloride according to a customary method. Then, the phenyl ester or acid chloride is directly reacted with an appropriate amine under heating or in a solvent such as benzene in the presence of pyridine, sodium carbonate or the like at room temperature or an elevated temperature. Thus, the intended coupler can be obtained. Further, the intended coupler can be obtained by reacting a free acid with a corresponding amine at room temperature in the presence of dicyclohexylcarbodiimide.

A coupler of the phenol type can be synthesized from a 1,4-dihydroxybenzene derivative in the same manner as described above. If desired, the intended coupler or its derivative may be prepared by blocking one of hydroxyl groups of the starting 1,4-dihydroxybenzene derivative with, for example, an acetyl group, a benzoyl group or the like by acylation to form a corresponding carbonylmethoxy derivative and hydrolyzing it with an acid such as hydrochloric acid, sulfuric acid or the like or an alkali such as sodium hydroxide, potassium hydroxide or the like. When the acylation is not proper, one of the hydroxyl group is benzylated to a benzyloxy group, the foregoing reaction is conducted and hydrogen gas is then introduced to effect reduction and remove the benzyl group.

Typical instances of the synthesis of the coupler of the present invention will now be described by reference to the following synthesis examples.

SYNTHESIS EXAMPLE 1

0.05 mole of 1-hydroxy-2-naphthoic acid was dissolved in 70 ml of DMF, and 10 ml of a 40% aqueous solution of sodium hydroxide was added dropwise to the solution while introducing nitrogen gas. Then, 0.05 mole of ethyl α-bromo-propionate was added dropwise and the mixture was agitated at 40° C. for 3 to 4 hours to effect reaction. After completion of the reaction, the reaction mixture was poured into ice-hydrochloric acid, and crystals were recovered by filtration and recrystallized from acetonitrile to obtain a compound having a melting point of 178° C. Then, 0.01 mole of 1-hydroxy-4-[1-(ethoxycarbonyl)-ethoxy]-2-naphthoic acid so obtained and 0.01 mole of N-(δ-2,4-di-tert-amylphenoxy)-butylamine were dissolved in 60 ml of dry dioxane, and 0.01 mole of dicyclohexylcarbodiimide was added to the solution. The reaction was conducted at room temperature under agitation for 2 hours. After completion of the reaction, the reaction mixture was filtered, and the filtrate was concentrated under reduced pressure and separated by column chromatography to obtain a compound having a melting point of 75° C. (the yield being 52%). From the results of the elementary analysis, it was confirmed that this compound was the compound (1) illustrated above.

SYNTHESIS EXAMPLE 2

0.05 mole of 1,4-dihydroxy-2-naphthoic acid was dissolved in 70 ml of DMF, and 10 ml of a 40% aqueous solution of sodium hydroxide was added dropwise to the solution while introducing nitrogen gas. Then, 0.05 mole of α-bromo-propionylethylamide dissolved in 15 ml of DMF was added dropwise and the reaction was conducted at 50° C. for 3 to 4 hours under agitation. After completion of the reaction, the reaction mixture was poured into ice-hydrochloric acid and crystals were recovered by filtration and recrystallized from acetonitrile to obtain a compound having a melting point of 192° C. Then, 0.01 mole of 1-hydroxy-4-[1-(ethylaminocarbonyl)ethoxy]-2-naphthoic acid so obtained was dissolved in 60 ml of dry dioxane, and 0.01 mole of dicyclohexylcarbodiimide was added to the solution. The reaction was conducted at 50° to 60° C. for 30 minutes under agitation. After completion of the reaction, the reaction mixture was filtered and dicyclohexylurea formed as a by-product was removed. The filtrate was concentrated under reduced pressure and n-hexane was added. Precipitated crystals were recovered by filtration and recrystallized from n-hexane to obtain a compound having a melting point of 95° C. (the yield being 65%). From the results of the elementary analysis, it was confirmed that the compound was the compound (2) illustrated above.

SYNTHESIS EXAMPLE 3

0.05 mole of 1,4-dihydroxy-2-naphthoic acid was dissolved in 70 ml of DMF, and 10 ml of a 40% aqueous solution of sodium hydroxide was added dropwise to the solution while introducing nitrogen gas. Then, 0.05 mole of diethyl α-bromo-succinate dissolved in 15 ml of DMF was added dropwise, and the reaction was conducted at 50° C. for 3 to 4 hours under agitation. After completion of the reaction, the reaction mixture was poured into ice-hydrochloric acid, and crystals were recovered by filtration and recrystallized from acetonitrile to obtain a compound having a melting point of 176° C. Then, 0.01 mole of the so obtained compound and 0.01 mole of n-dodecylbutylamine were dissolved in 60 ml of dry dioxane, and 0.01 mole of dicyclohexylcarbodiimide was added to the solution and the reaction was carried out at 50° C. for about 30 minutes. After completion of the reaction, the reaction mixture was filtered and dicyclohexyl urea formed as a by-product was removed. The filtrate was concentrated under reduced pressure and separated by column chromatography to obtain a compound having a melting point of 68° C. (the yield being 35%). From results of the elementary analysis and the like, it was confirmed that the so obtained compound was the compound (4) illustrated above.

SYNTHESIS EXAMPLE 4

1-Hydroxy-4-[1-(4-nitro-anilinocarbonyl)-2-ethylaminocarbonylethoxy]-N-[δ-(3-n-dodecyloxy-phenoxy)-butyl]-2-naphthamide prepared by the same reaction described in the preceding Synthesis Examples was reduced with zinc and hydrochloric acid according to a customary method. The resulting amino compound was diazotized and coupled in an alkaline state with disodium 2-hydroxy-3,6-disulfonate to obtain a compound having a melting point higher than 300° C. (the yield being 60%). From results of the elementary analysis and the like, it was confirmed that this compound was the compound (5) illustrated above.

Various couplers can be synthesized according to the above-mentioned synthesis method. Results of the elementary analysis of couplers illustrated above among couplers synthesized according to the foregoing method are described below.

| Coupler No. | Elementary Analysis Values (%) | | | | | |
|---|---|---|---|---|---|---|
| | Calculated Values | | | Found Values | | |
| | C | H | N | C | H | N |
| 1 | 73.06 | 8.35 | 2.37 | 72.93 | 8.67 | 2.22 |
| 2 | 73.18 | 8.53 | 4.74 | 73.24 | 8.45 | 4.72 |
| 3 | 71.51 | 7.65 | 4.17 | 71.81 | 7.51 | 4.49 |
| 4 | 68.48 | 8.34 | 2.58 | 68.36 | 8.49 | 2.67 |
| 5 | 58.55 | 5.63 | 6.21 | 58.29 | 5.76 | 6.29 |
| 6 | 74.19 | 7.86 | 6.18 | 74.09 | 7.43 | 6.42 |
| 7 | 69.02 | 7.45 | 3.83 | 68.92 | 7.75 | 3.96 |
| 8 | 49.33 | 4.89 | 2.62 | 49.18 | 4.72 | 2.15 |
| 9 | 64.33 | 6.75 | 3.75 | 64.53 | 6.48 | 3.92 |
| 10 | 75.36 | 8.26 | 2.44 | 75.65 | 8.41 | 2.71 |
| 11 | 66.19 | 5.79 | 9.65 | 66.08 | 5.53 | 9.69 |
| 12 | 69.12 | 8.10 | 1.68 | 68.76 | 8.49 | 1.37 |
| 13 | 67.05 | 5.33 | 4.12 | 67.24 | 5.62 | 4.30 |

Couplers of the present invention prepared according to the above method have a much higher dye forming speed at the color developing step than conventional 4-equivalent couplers and than 2-equivalent couplers containing as the split-off group an aryloxy group such as a phenoxy or nitrophenoxy group or an ester-linked group such as an acetoxy or benzoyloxy group. Further, as compared with conventional couplers having a similar structure, couplers of the present invention are more readily dispersible in photographic protective colloids such as gelatin. Oil-soluble couplers of the present invention have an excellent solubility in coupler solvents. Couplers of the present invention having a hydrophilic group shown an excellent adaptability to Fisher dispersions. So-called "outer type" couplers of the present invention which are to be used outside photosensitive materials can be very easily added to a color developer or the like. Because of these favorable properties, when couplers of the present invention are incorporated into photosensitive layers of photographic sensitive materials as so-called "inner type" couplers, the thickness of the photosensitive layer can be remarkably reduced, and the sharpness and other characteristics of the resulting color image can be highly improved. Further, the couplers of the present invention have no adverse influences to the color development, and particularly, they are characterized that they do not cause color stain or other defects due to their good reactivity.

Furthermore, a dye obtained by using the coupler of the present invention has excellent absorption characteristics as pointed out hereinbefore.

The coupler of the present invention can be applied in various manners by selecting appropriately the combination of the base structure and the split-off group. For example, when the cyan coupler residue has a water-soluble group such as a sulfonic or carboxylic group, the coupler has a diffusible property, and when the split-off group per se is diffusible, the coupler can be used as a diffusible coupler for the so-called outer type photographic technique wherein it can be incorporated into a liquid color developer. As such coupler, there can be mentioned the coupler (8) illustrated above.

Further, the coupler of the present invention having a diffusible cyan coupler residue and a non-diffusible split-off group such as a long-chain aliphatic hydrocarbon residue, e.g., octadecyl group, can also be used for the outer type photographic technique if the non-diffusibility of the split-off group is moderate and the entire structure where the cyan coupler residue is bonded to the split-off group at the active position is diffusible.

In addition to the above-mentioned coupler (8), there may be preferably employed couplers (11) and (13) illustrated above as the outer type coupler.

According to the outer type photographic technique, as is well known in the art, a coupler is incorporated into a liquid color developer, and when a coupler-free photosensitive material, especially a black-and-white silver halide photosensitive material (occasionally designed as the outer type photosensitive material), is developed by such color developer, the color developer and diffusible coupler penetrate into the photosensitive material, and the color developer reacts with the diffusible coupler in the presence of a silver halide having a development nucleus, whereby a dye that is finally a dye image is formed. In the case where a multicolored image is prepared, the color development is conducted in succession with different color developers containing different couplers (for example, cyan, magenta and yellow couplers).

Such liquid color developer may comprise, in addition to the color developer and the coupler, various photographic additives customarily used for a liquid color developer composition, such as alkali metal sulfites, carbonates, bisulfites, bromides and iodides. A typical formulation of such liquid developer is as follows:

| Color developer | 1 to 5 g |
|---|---|
| Anhydrous sodium sulfite | 1 to 3 g |
| Anhydrous sodium carbonate | 10 to 60 g |
| Potassium bromide | 0.5 to 1.5 g |
| Coupler | 1 to 3 g |
| Water to make 1 liter | |

The liquid color developer containing the coupler of the present invention, especially such outer type coupler as mentioned above, has a higher solubility than conventional couplers, and it has the above-mentioned excellent characteristics.

A coupler which has a diffusible cyan coupler residue and a diffusible split-off group but which is non-diffusible as a whole, a coupler which has a non-diffusible cyan coupler residue and a diffusible split-off group and which is non-diffusible as a whole, and a coupler which has a non-diffusible cyan coupler residue and a diffusible split-off group and which is diffusible as a whole are suitably used for the diffusion transfer photographic process. In order to render these groups diffusible, it is possible to adopt techniques of selecting low-molecular-weight groups and/or introducing water-soluble groups such as mentioned above, for example, a sulfonic group. In order to render these groups non-diffusible, it is possible to adopt techniques of introducing a long-chain aliphatic hydrocarbon residue and/or selecting a relatively high-molecular-weight group.

Even a coupler having a diffusible cyan coupler residue and a diffusible split-off group can be used for the diffusion transfer process if the chemical portion unnecessary for formation of an image at the color developing step is non-diffusible. More specifically, if a hydroquinone residue, a resorcinol residue or the like is introduced into one of these diffusible cyan coupler residue and split-off group directly or through a suitable linking group, the resulting coupler can be effectively used for the diffusion transfer process. This technique can be applied to couplers in which the diffusibility characteristics of the cyan coupler residue and split-off group differ from those mentioned above. When the diffusion transfer process is adopted, an image is formed either by a method in which a cyan dye formed by the reaction between the cyan coupler residue and the color developer is utilized for the image formation or by a method in which the split-off group isolated during the color development is utilized for the image formation. In the former method it is necessary that the cyan dye obtained should be diffusible and in the latter method it is necessary that a compound formed by isolation of the split-off group from the active position should be diffusible. When this isolated compound is utilized, it is also necessary that the compound should be colored. For example, the compound should contain a coloring portion, for example, an azo dye. Split-off groups of this type are represented by, for example, the following general formulas [VII] and [VIII]:

wherein D and D' stand for a dye residue.

In the above general formulas [VII] and [VIII], the dye residues are preferably water-soluble and preferred examples are monovalent residues of azo dyes, azomethine dyes, indeaniline dyes, indophenol dyes and anthraquinone dyes.

As the coupler suitable for the diffusion transfer process, there can be mentioned, for example, couplers (5) and (12) illustrated above.

In the diffusion transfer process, as is well known in the art, a photosensitive material and an image-receiving material are used in combination. According to this photographic technique, after the photosensitive material has been exposed to light, it is superposed on the image-receiving material at the developing step at latest, whereby an image is formed on the image-receiving material. For example, a coupler-containing silver halide photosensitive material and an image-receiving material having an image-receiving layer on a support through a sub layer, an inter layer and the like are used in combination, and after the silver halide photosensitive material has been exposed to light, the photosensitive layer of the silver halide photosensitive material is superposed on the image-receiving layer of the image-receiving material optionally through a protective layer. A liquid color developer penetrates between the two layers to effect development and a dye formed in the photosensitive layer is diffused and transferred onto the image-receiving layer. Finally, the image-receiving layer is peeled from the photosensitive material and a color image is formed on the thus peeled image-receiving material. Various methods are known as this diffusion transfer photographic process. For example, a photosensitive material is integrated with an image-receiving material, whereby the steps of placing the photosensitive material on the image-receiving material and peeling the image-receiving material from the photosensitive material are omitted. In this case, if a boundary layer between the image-receiving material and photosensitive material or a layer adjacent thereto is an opaque layer, a support of the photosensitive material should be transparent and the photosensitive material is exposed to light through this transparent support. If the boundary layer or adjacent layer is substantially transparent, the finally obtained image may be adversely affected by the image in the photosensitive material, and therefore at least one of these layers should be opacified at the steps subsequent to the light exposure. For example, opacification is conducted at the color developing step. In the integrated combination of this type including a photosensitive material and an image-receiving material, at least one of supports of the image-receiving material and the photosensitive material must be transparent, and exposure is conducted through the transparent support. After the light exposure, a liquid color developer penetrates into the interface between the photosensitive material and the image-receiving material or in the vicinity of this interface, whereby an image is formed in the image-receiving layer.

According to another type of the diffusion transper process, a liquid color developer is included in an image-receiving material, and the development and image transfer can be accomplished only by superposing an exposed photosensitive material to the image-receiving material.

Couplers of the present invention can be effectively used for any type of the diffusion transfer methods. In general, the coupler of the present invention is included into a photosensitive layer and in this case, a silver halide photosensitive material is preferred as the photosensitive layer. In general, the coupler is incorporated in an amount of about 0.07 mole to about 0.7 mole, preferably 0.1 to 0.4 mole, per mole of the silver halide.

A so-called inner type coupler is usually employed in such a state as being incorporated into a photosensitive material, especially a silver halide photosensitive material. Preferably, a non-diffusible coupler is used so as to prevent other layers from being adversely affected by the coupler. Among the above-mentioned couplers to be used for the diffusion transfer process, those which are non-diffusible can be effectively used as such inner type coupler. Couplers having a non-diffusible coupler residue are especially preferred. In this case, the split-off group may be either diffusible or non-diffusible.

Couplers (1), (2), (3), (4), (5), (6), (7), (9) and (10) are preferably used as the coupler of this type.

Some of inner type couplers are substantially colorless, and they form a dye by reaction with an oxidation product of the color developer formed during the color development. Other couplers of this type are so-called colored couplers and they can be used for color adjustment according to the masking method. The coupler (5) is preferably used as the coupler of this type. According to this masking method, the color of the colored coupler disappears at the color development or the colored coupler is removed from the system of the photosensitive material, and simultaneously, a cyan dye is formed by reaction with the color developer. Thus, the color of the colored coupler is utilized for color adjustment. In general, this colored coupler is used in combination with a substantially colorless coupler.

These inner type couplers are divided into two groups; one containing a hydrophilic group in the molecule and the other containing an oleophilic group in the molecule. For example, when these couplers are incorporated into coating compositions for formation of photosensitive layers, the former group of couplers, namely so-called Fischer dispersion type couplers, are incorporated as a solution or a dispersion in an alkaline solution, and the latter group of couplers, namely so-called protect type couplers, are incorporated as a solution in a coupler solvent. Typical example of the coupler of the present invention belonging to the former group is coupler (7) illustrated above, and when the above-mentioned dispersing method is adopted, these couplers of the present invention have a much better dissolving property than the conventional couplers and they provide various advantages. For example, a dye image of a higher concentration can be obtained, the transparency of the layer can be highly improved, and the resolving power can be remarkably enhanced.

In general, the coupler of the present invention is incorporated into the photosensitive material in an amount of about 0.07 mole to about 0.7 mole, preferably 0.1 to 0.4 mole, per mole of the silver halide. When the coupler is used for color adjustment or used for improving the characteristics of other couplers, the coupler of the present invention is used in an amount of about 0.01 mole to about 0.1 mole, preferably about 0.03 to about 0.07 mole, per mole of the silver halide.

As illustrated hereinbefore, the coupler of the present invention can be used for attaining various objects and shows excellent characteristics with respect to each use.

A silver halide photosensitive material is preferred as the photosensitive material to which the coupler of the present invention is applied, and the coupler of the present invention can be used for various silver halide photosensitive materials, for example, a silver halide photosensitive material to be used for the above-mentioned diffusion transfer process, an ordinary negative photosensitive material, an ordinary reversal photosensitive material, an ordinary positive photosensitive material, a direct positive photosensitive material and special silver halide photosensitive materials (for printing, X-ray photography, high resolving power photography, infrared photography and ultraviolet photography).

As the silver halide to be used for these silver halide photosensitive material, there can be mentioned, silver chloride, silver iodide, silver iodobromide, silver chlorobromide and silver chloroiodobromide. These silver halides are prepared according to various methods, for example, the neutral method, the ammonia method, the simultaneous mixing method, the conversion method and the like, and a suitable preparation method is selected depending on the kind of the photosensitive material. In case of a mixed silver halide, the mixing ratio of two or more of silver halides is appropriately chosen. For example, in case of a silver halide having a relatively low sensitivity and a finer particle size, silver chloride is used as the main component, but in case of a coupler having a relatively high sensitivity, the content of silver chloride is reduced. The silver halide to be used for a direct positive photosensitive material includes a Herschel reversal type and a solarization type. In general, this silver halide is optically or chemically sensitized to impart a suitable fog to silver halide grains. More specifically, the silver halide is chemically sensitized with active gelatin, a sulfur sensitizer such as allyl thiocarbamide, thiourea, cystine or the like, a selenium sensitizer, a reducing sensitizer such as a stannous salt, a polyamine or the like, a noble metal sensitizer, especially a gold sensitizer, such as potassium aurithiocyanate, potassium chloroaurate, 2-aurosulfobenzothiazole methochloride, a water-soluble salt of ruthenium, rhodium or iridium, ammonium chloropalladate, potassium chloroplatinate, sodium chloropalladite or the like (some acting as a sensitizer or a fog inhibiting agent according to the amount used), or a combination of two or more of the foregoing sensitizers, for example, a combination of a gold sensitizer and a sulfur sensitizer or a combination of a gold sensitizer and a selenium sensitizer.

This silver halide can be optically sensitized to a desired wavelength region. For example, it can be optically sensitized (supersensitized) with a cyanine dye such as a zeromethine dye, a monomethine dye, a dimethine dye or a trimethine dye, a merocyanine dye or a combination of two or more of these dyes.

A photosensitive layer is formed by dispersing the silver halide into a suitable protective colloid. In general, gelatin is used for formation of a photosensitive layer and other layers such as an inter layer, a protective layer, a filter layer, an image-receiving layer, a pH-adjusting layer (to be used, for example, as a layer to be disposed below the image-receiving layer) and the like. In addition, colloidal alubmin, cellulose derivatives and synthetic resins such as polyvinyl compounds (for example, polyvinyl alcohol) can be used singly or in combination. Still further, acetyl cellulose having an acetyl content of 19 to 26% and a water-soluble ethanolamine cellulose acetate may be used in combination with the foregoing protective colloids.

As the support of the photosensitive material, there can be employed films and sheets of such substrates as paper, laminated paper (for example, a laminate of polyethylene and paper), glass, cellulose acetate, cellulose nitrate, polyester, polycarbonate, polyamide, polystyrene and polyolefin. These substrates can be subjected to various surface treatments such as hydrophilic treatments so as to improve layer adhesion. For example, there can be performed saponification, corona discharge, subbing and setting.

The photosensitive material comprises at least a support and a photosensitive material formed thereon. In general, however, the photosensitive material has a multilayer structure including other suitable layers disposed at suitable positions depending on the foregoing purposes of provision. For example, a color photosensitive material may include at least two photosensitive layers sensitized to different wavelength regions, and these photosensitive layers may contain couplers providing different color dyes.

The coupler of the present invention forms a cyan dye when its cyan coupler residue is utilized. In this case, the cyan coupler is generally used for a photosensitive material in combination with 2-equivalent or 4-equivalent couplers, for example, a magenta coupler such as 5-pyrazolone and a yellow coupler containing an active methylene group interposed between two carbonyl groups. In case of an inner type photosensitive material, these couplers are incorporated into photosensitive layers sensitized to suitable wavelength regions, respectively. In case of pseudocolor photosensitive material, the coupler of the present invention may be used singly or in combination of the same kind of a coupler, and in this case, the relation between the sensitized wavelength region and the coupler is not in agreement with this relation in an ordinary color photosensitive material.

The photosensitive layer sensitized to a certain wavelength region may comprise two or more of layers. These layers may be different with respect to the sensitivity, and different types of couplers, for example, a 2-equivalent coupler and a 4-equivalent coupler, which form the same color, may be incorporated into these layers, respectively. This technique is generally adopted for improving the resolving power and the sensitivity.

As pointed out hereinbefore, the coupler of the present invention may be used in combination with other 2-equivalent or 4-equivalent coupler. For example, the coupler of the present invention can be used in combination with a 2-equivalent coupler such as a so-called colored coupler (for example, a coupler in which a split-off group including an azo group as the linking group is bonded to the active point of the coupler) or a so-called DIR coupler (a coupler releasing a development inhibitor at the color developing step, for example, a coupler in which a thio group-containing split-off group is bonded to the active point of the coupler).

Various photographic additives may be incorporated into a photosensitive layer and/or other layers (such as inter, sub, filter, protective and image-receiving layers). As such photographic additives, there can be mentioned, for example, stabilizers such as mercury compounds, triazoles, azaindenes, zinc salts and cadmium salts, sensitizers such as quarternary ammonium salts and polyethylene glycols, film property-improving agents such as glycerin, hydroxyalkanes, ethylene-bis-glycol esters and polymer emulsions, hardeners such as formaldehyde, halogen-substituted fatty acids, disulfonic chloride, bis-aziridine and ethylene imines, spreading agents such as saponin, polyethylene glycol lauryl monoether, polyethylene glycol oleyl monoether and sulfated and alkylated polyethylene glycol salts, organic solvents such as coupler solvents (high-boiling solvents and low-boiling solvents, for example, dibutyl phthalate, tricresyl phosphate, acetone, methanol, ethanol and ethyl cellosolve), so-called DIR compounds capable of releasing a color development inhibitor and forming a substantially colorless compound at the color developing step, antistatic agents, defoamers, ultraviolet absorbers, fluorescent whitening agents, anti-slip agents, matting agents, anti-halation agents and anti-irradiation agents. These additives may be used singly or in combination.

An image-receiving layer which is formed separately from a photosensitive material as mentioned above and is used for the diffusion transfer process in combination with the photosensitive material includes at least a support such as mentioned above and an image-receiving layer formed on the support, and it may include other layers such as protective, sub and pH-adjusting layers according to need. Further, photographic additives such as exemplified above may be incorporated in these layers according to need. For example, in order to prevent re-diffusion or irradiation of the diffusible dye diffused from the photosensitive layer during the color development, it is preferred that a compound capable of catching the dye or rendering the dye non-diffusible be incorporated into the image-receiving layer. Such compound may be incorporated into a layer adjacent to the image-receiving layer. For example, mordants such as polymers of aminoguanidine derivatives of vinylmethylketone as disclosed in the specification of U.S. Pat. No. 2,882,156 and mordants disclosed in the specification of U.S. Pat. No. 3,271,148 and the specification of U.S. Pat. No. 3,271,147. Such pH-adjusting agents as inorganic and organic acids also are typical examples of such compound to be incorporated in the image-receiving layer or the layer adjacent thereto.

A liquid color developer which is used for color development of the exposed photosensitive material comprises a color developer as the main ingredient. Typical color developing agents are aromatic primary amino compounds such as p-phenylene diamines. For example, there are employed diethyl-p-phenylene diamine hydrochloride, monomethyl-p-phenylene diamine hydrochloride, dimethyl-p-phenylene diamine hydrochloride, 2-amino-5-diethylaminotoluene hydrochloride, 2-amino-5-(N-ethyl-N-dodecylamino)-toluene, N-ethyl-N-$\beta$-methanesulfonamidoethyl-3-methyl-4-aminoaniline sulfate, N-ethyl-N-$\beta$-methanesulfonamidoethyl-4-aminoaniline and 4-N-ethyl-N-$\beta$-hydroxyethylaminoaniline, N-ethyl-N-$\beta$-methoxyethyl-3-methyl-4-aminoaniline p-toluenesulfonate, N-ethyl-N-[2-(2-methoxyethoxy)ethyl]-3-methyl-4-aminoaniline p-toluenesulfonate, N-ethyl-N-{2-[2-(2-methoxyethoxy)ethoxy]ethyl}-3-methyl-4-aminoaniline p-toluenesulfonate, N-ethyl-N-[2-{2-(2-[2-(2-methoxyethoxy)ethoxy]ethoxy}ethyl]-3-methyl-4-aminoaniline p-toluenesulfonate.

These color developers may be used singly or in combination, or they may be used, if desired, in combination with a black-and-white developer such as hydroquinone. The liquid color developer generally contains an alkaline agent such as sodium hydroxide, ammonium hydroxide, sodium carbonate, sodium sulate, sodium sulfite or the like. It may further comprise various additives, for example, an alkali metal halide such as potassium bromide and a development adjusting agent such as citrazinic acid. In a certain diffusion transfer process, this liquid color developer is incorporated in advance into an image-receiving layer. In this case, it is possible to adopt a technique in which the color developer is separated from the alkaline agent, and only the alkaline agent or the color developer is incorporated into the image-receiving layer and it is treated with the other component at the developing step.

The coupler of the present invention forms a cyan dye by reacting with an oxidation product of the color developer formed when the silver halide is developed with the liquid color developer, and some couplers of the present invention form other dyes (including a cyan dye).

In the case where the silver halide or developed silver in the photosensitive material is to be removed after this color development, a fixing solution, a bleaching solution, a combination of a fixing solution and a bleaching solution and a bleaching-fixing solution are, in general, used. This treatment is carried out in combination with other various treatments such as water-washing, stopping and stabilization. For the fixing purpose, there are employed solvents for silver halide such as sodium thiosulfate and ammonium thiosulfate, and for the bleaching, there are employed potassium ferricyanide, ferric ammonium ethylenediamine tetraacetate, and sodium ethylenediamine tetraacetate.

The coupler of the present invention having the above structure is much excellent over conventional 2-equivalent couplers in photographic characteristics, as pointed out hereinbefore.

The present invention will now be described in detail by reference to the following examples that by no means limit the scope of the invention.

EXAMPLE 1

A coupler indicated in Table 1 was used, and 10 g of the coupler was added to a liquid mixture of 20 ml of dibutyl phthalate and 60 ml of ethyl acetate, and the temperature was elevated at 60° C. to dissolve the coupler completely. The resulting solution was mixed with 5 ml of a 10% aqueous solution of Alkanol B (alkylnaphthalene sulfonate manufactured by Du Pont) and 200 ml of a 5% aqueous solution of gelatin, and the mixture was emulsified by using a colloid mill to form a coupler dispersion.

Then, the so prepared dispersion was added to 500 g of a high speed negative silver iodobromide (containing 6.0 mole% of silver iodide) gelatin emulsion, and the mixture was coated on a cellulose triacetate film base and dried.

The so prepared sample was subjected to light exposure through an optical wedge and developed at 20° C. for 10 minutes with a liquid color developer having the following formulation:

| | |
|---|---|
| N-Ethyl-N-$\beta$-methanesulfonamidoethyl-3-methyl-4-aminoaniline sulfate | 5.0 g |
| Anhydrous sodium sulfite | 2.0 g |
| Sodium carbonate (monohydrate) | 50.0 g |
| Potassium bromide | 1.0 g |
| Sodium hydroxide | 0.55 g |
| Benzyl alcohol | 4.0 ml |
| Water to make 1 liter | |

The sample was then subjected to the stopping and fixing treatment according to a customary method, washed with water for 10 minutes and bleached at 20° C. for 5 minutes with a bleaching solution having the following formulation:

| | |
|---|---|
| Potassium ferricyanide | 100 g |
| Potassium bromide | 50 g |
| Water to make 1 liter | |

Then, the sample was washed with water for 5 minutes and subjected to the fixing treatment at 20° C. for 5 minutes with a fixing solution having the following formulation:

| | |
|---|---|
| Sodium thiosulfate (heptahydrate) | 250 g |
| Water to make 1 liter | |

Then, the sample was washed with water again for 25 minutes and dried.

Photographic characteristics of the so treated sample was measured to obtain results shown in Table 1.

Table 1

| Sample No. | Coupler used | Relative speed | Gamma ($\gamma$) | Maximum density ($D_{max}$) | Maximum absorption wavelength ($\lambda max$) | Image Light fastness | Moisture fastness |
|---|---|---|---|---|---|---|---|
| 1 | Coupler (1) | 131 | 1.17 | 2.22 | 700 nm | 91% | 74% |
| 2 | Coupler (4) | 140 | 1.20 | 2.33 | 700 nm | 92% | 76% |
| 3 | Comparative coupler (1) | 100 | 1.00 | 1.95 | 700 nm | 90% | 68% |

In the Table, the relative speed is expressed based on the speed of the sample 3 formed by using the comparative coupler (1), which is evaluated as 100. The comparative coupler (1) has a structure described below. The light fastness is expressed in terms of the ratio (%) of the residual density after 16 hours' exposure to a Xenon Fade-O-Meter to the density before the exposure. The moisture fastness is expressed in terms of the ratio (%) of the residual density after 2 weeks' storage at a relative humidity of 80% and a temperature of 50° C. to the density before the exposure.

The structure of the comparative coupler (1) (disclosed in the specification of U.S. Pat. No. 2,474,293) has the following structure:

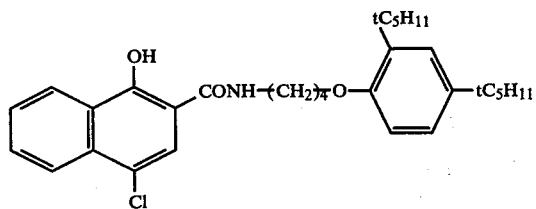

As will be apparent from the results shown in Table 1, the coupler of the present invention has excellent photographic characteristics (high speed, excellent light fastness and excellent moisture fastness), and the sample formed by using the coupler of the present invention provides a color image having high sharpness.

When the coupler (2) was used instead of the couplers (1) and (4), it was found that the coupler (2) was an inner type coupler having excellent photographic characteristics similar to those of the couplers (1) and (4).

EXAMPLE 2

To a liquid mixture of 20 ml of dibutyl phthalate and 60 ml of ethyl acetate was added 10 g of the coupler (10), and the temperature was elevated at 60° C. to dissolve the coupler completely. The resulting solution was mixed with 5 ml of a 10% aqueous solution of Alkanol B and 200 ml of a 5% aqueous solution of gelatin, and the mixture was emulsified by a colloid mill to form a coupler dispersion.

The so formed dispersion was added to 500 g of a high speed red-sensitive, silver iodobromide emulsion (containing 4.0 mole % of silver iodide), and the mixture was coated on a cellulose acetate film base and dried to obtain a photographic sensitive material having stable coating.

The photosensitive material was exposed to light in the same manner as described in Example 1 and developed at 21° C. for 12 minutes with a liquid developer having the following formulation:

| | |
|---|---|
| Method | 3.0 g |
| Anhydrous sodium sulfite | 50.0 g |
| Hydroquinone | 6.0 g |
| Anhydrous sodium carbonate | 40.0 g |
| Potassium bromide | 3.5 g |
| Potassium thiocyanide | 2.0 g |
| Water to make 1 liter | |

Then, the sample was subjected to stopping, hardening and water washing treatments according to customary procedures, and then it was subjected to the secondary exposure under white light.

Then, the sample was subjected to the color development at 21° C. for 13 minutes with a liquid color developer having the following formulation:

| | |
|---|---|
| N,N-Diphenyl-2-methyl-p-phenylene diamine | 3.0 g |
| Anhydrous sodium sulfite | 4.0 g |
| Sodium carbonate (monohydrate) | 20.0 g |
| Potassium bromide | 2.0 g |
| Water to make 1 liter | |

Then, the sample was subjected to stopping, water-washing, bleaching and fixing treatments according to customary procedures, and washed with running water for 20 minutes and dried to obtan a positive cyan dye image being excellent in transparency and having an absorption maximum at 700 nm.

From the foregoing illustration, it will readily be understood that the coupler of the present invention shows excellent photographic characteristics when it is used for a reversible photosensitive material.

EXAMPLE 3

In a liquid mixture of 20 ml of tricresyl phosphate and 60 ml of ethyl acetate was dissolved 20 g of a coupler indicated in Table 2, and a coupler dispersion was prepared from the solution in the same manner as described in Example 1. The coupler dispersion was added to 100 ml of a high speed silver iodobromide emulsion and the mixture was coated on a film base and dried to form a photosensitive material.

The photosensitive material was exposed to light according to a customary method and developed at 38° C. for 3 minutes and 15 seconds with a liquid color developer having the following formulation:

| | |
|---|---|
| N-Ethyl-N-($\beta$-hydroxyethyl)-3-methyl-4-aminoaniline hydrochloride | 5.0 g |
| Anhydrous sodium sulfite | 2.0 g |
| Sodium carbonate | 50.0 g |
| Potassium bromide | 1.0 g |
| Sodium hydroxide | 0.55 g |
| Water to make 1 liter | |

Then, the sample was bleached at 38° C. for 6 minutes with a bleaching solution having the following formulation:

| Disodium ethylenediaminetetraacetate | 40.0 g |
|---|---|
| Ferric chloride | 30.0 g |
| Sodium carbonate (monohydrate) | 20.0 g |
| Potassium bromide | 30.0 g |
| Water to make 1 liter | |

Then, the sample was subjected to water-washing, fixing and stabilizing treatments according to customary procedures to obtain a positive image having an absorption maximum at 520 to 535 nm and a cyan dye image having an absorption maximum at 700 nm.

Photographic characteristics of the sample were measured to obtain results shown in Table 2.

In the Table, the relative speed is expressed based on the speed of the sample formed by using the following comparative coupler (2), which is evaluated as 100. Comparative Coupler (2) (disclosed in the specification of U.S. Pat. No. 3,034,892):

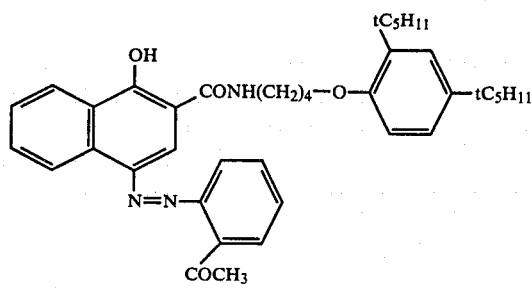

Table 2

| Sample No. | Coupler used | Relative speed | Maximum density ($D_{max}$) | Maximum absorption wavelength ($\lambda_{max}$) | Maximum absorption wavelength of mask ($\lambda_{max}$) |
|---|---|---|---|---|---|
| 4 | Coupler (5) | 138 | 1.8 | 700 | 520 |
| 5 | Comparative coupler (2) | 100 | 1.6 | 700 | 500 |

In the above Table, the maximum absorption wavelength of the mask is the maximum absorption wavelength of the color of the coupler per se.

In this Example, the coupler of the present invention is applicable to the so-called masking method. As will be apparent from the results shown in the above Table, the coupler shows excellent photographic characteristics also in this case, and the coupler of the present invention is remarkably improved over the conventional coupler with respect to the sensitivity and density and provides an excellent dye image having an improved sharpness.

EXAMPLE 4

Coupler (7) was incorporated into a high speed negative silver iodobromide emulsion according to the Fischer dispersion method (the amount used of the coupler was 0.2 mol per mole of the silver halide), and the emulsion was coated on a cellulose triacetate film base and dried according to a customary method.

The so obtained sample was exposed to light and treated at 24° C. for 3 minutes with an alkaline liquid developer having the following formulation:

| Sodium sulfite | 2.0 g |
|---|---|
| 4-N-Ethyl-Nβ-hydroxyethylamino-aniline | 11.0 g |
| Water to make 1 liter | |

During the above development, the photosensitive layer of the sample was superposed on an image-receiving of an image-receiving material containing in the image-receiving layer dimethyl-β-hydroxyethyl-γ-stearoamidopropylammonium hydrodiene phosphate, and after the development, the image-receiving material was peeled from the photosensitive material. A sharp negative cyan image excellent in photographic characteristics was formed on the image-receiving material. Thus, it was confirmed that the coupler of the present invention is excellent also as the coupler for use in the diffusion transfer color photography.

EXAMPLE 5

Coupler (8) was dissolved in methanol and by using this solution, an outer type liquid color developer having the following formulation was prepared:

| N,N-Diethyl-2-methyl-p-phenylene diamine | 2.0 g |
|---|---|
| Anhydrous sodium sulfite | 2.0 g |
| Sodium carbonate (monohydrate) | 20.0 g |
| Potassium bromide | 1.0 g |
| Coupler (8) | 2.0 g |
| Water to make 1 liter | |

A sample formed by coating a high speed silver iodobromide emulsion on a subbed polyethylene terephthalate film was exposed to light and developed at 24° C. for 3 minutes with the above outer type liquid color developer.

The developed sample was washed with water for 4 minutes, bleached for 5 minutes, washed with water for 5 minutes, fixed for 5 minutes, water-washed for 30 minutes and dried according to customary procedures. There was obtained a cyan image having an absorption maximum at 700 nm and a high spectral characteristic and being excellent in other photographic characteristics.

When the above procedures were repeated in the same manner by using coupler (11) instead of the above coupler (8), a similarly excellent dye image having a maximum absorption at 700 nm was obtained.

Thus, it was confirmed that the coupler of the present invention is excellent as the outer coupler.

EXAMPLE 6

Dispersion A

In a mixed solvent of 22 ml of tricresyl phosphate and 6.0 ml of ethyl acetate were dissolved 0.15 g of coupler (5) and 2.0 g of a known coupler, 1-hydroxy-N-[δ-(2,4-di-t-amylphenoxy)butyl]-2-naphthamide, and from this solution, a coupler dispersion was prepared in the same manner as described in Example 1.

Dispersion B

To the dispersion A was further added 0.20 g of a known DIR compound, 2-(1-phenyl-5-tetrazolylthio)-4-[2-(2,4-di-t-amylphenoxy)acetamido]-indanone.

Dispersion C

In the same manner as described above with respect to the dispersion B, this dispersion was prepared by using, instead of the above DIR compound, 0.1 g of a known DIR coupler, 1-hydroxy-4-(1-phenyl-5-tetrazolylthio)-2-(2-tetradecyloxyphenyl)-naphthamide.

Dispersion D

In the same manner as described above with respect to the dispersion B, this dispersion was prepared by using the known comparative coupler (2) instead of the coupler (5) of the present invention.

Each dispersion was added to 100 ml of a high speed, red-sensitive silver iodobromide emulsion (containing 7.0 mole % of silver iodide), and the mixture was coated on a film base and dried. Thus, there were prepared four photosensitive materials.

These photosensitive materials were exposed to light according to a customary method and then treated in the same manner as described in Example 3. The photosensitive material B was superior to the materials A, C and D with respect to the gradation in the resulting dye image. Further, the dye image formed by using the photosensitive material B was excellent in the graininess and the sharpness. The results are shown in Table 3.

Table 3

| Photo-sensitive material | Fog | Relative speed | Gamma | Graininess (RMS) | Sharpness (U 0.5) |
|---|---|---|---|---|---|
| A | 0.22 | 100 | 1.00 | 53 | 50 |
| B | 0.11 | 97 | 0.72 | 40 | 40 |
| C | 0.13 | 92 | 0.71 | 43 | 42 |
| D | 0.14 | 95 | 0.72 | 45 | 43 |

The RMS value is a value obtained multiplying the standard deviation of the change of the density value caused when scanned by a round microdensitometer having a scanning diameter of 25μ, by 1000. The U 0.5 value is a space frequency value at which the MT factor is reduced to 50%.

What we claim is:

1. A process for forming a cyan dye image, which comprises developing an imagewise exposed light-sensitive silver halide color photographic material having a support and at least one silver halide emulsion layer thereon with a color developer containing a color developing agent in the presence of a 2-equivalent cyan coupler of the following formula (II) or (III):

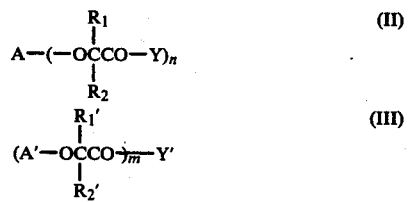

wherein A and A' each represent, at the active point of the cyan coupler, a cyan coupler residue of the formula:

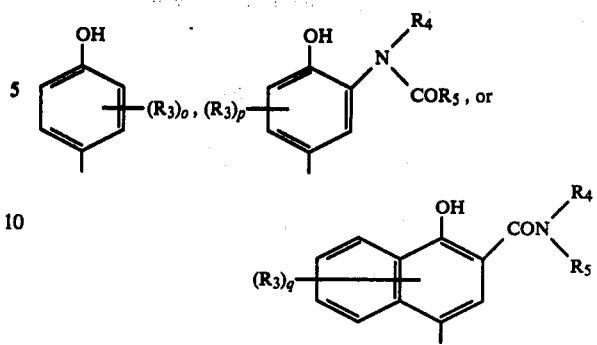

wherein $R_1$, $R_2$, $R_1'$ and $R_2'$ each represent a hydrogen atom, or an organic group selected from the group consisting of nitro, hydroxy, cyano, carboxy, sulfo, thienyl, pyridyl, quinolyl, oxadiazolyl, morpholino, piperazyl, imidazolyl, pyridinylene, quinolylene, monovalent or divalent alkyl, alkenyl, aryl, alkoxy, aryloxy, arylthio, arylazo, acylamino, carbamoyl, carboxylic acid ester, acyl, acyloxy, sulfonamido, sulfamoyl and sulfonyl, with the proviso that at least one $R_1$ and $R_2$ or $R_1'$ and $R_2'$ is an organic group as defined above; Y is selected from the group consisting of monovalent or divalent alkoxy group, phenoxy group, naphthoxy group, aliphatic hydrocarbon amino residue, mercapto group, pyridylene, quinolylene, a divalent aliphatic hydrocarbon, and an aromatic hydrocarbon residue; Y' is selected from the group consisting of a divalent, trivalent or higher valent aliphatic hydrocarbon residue, aromatic hydrocarbon residue, pyridylene, quinolylene, alkylenedioxy group, arylenedioxy group, alkylenediamino residue, arylenediamino residue, and a divalent or trivalent composite group including two or more linked groups selected from the foregoing groups; and $R_1$ and $R_2$ or $R_1'$ or $R_2'$, may be bonded to the carbon atom of the carbonyl group through the group Y or Y' to form a ring, with the proviso that in this instance $R_1$ or $R_2$ and Y represent the divalent group, and $R_1'$ or $R_2'$ represents the divalent group, Y' represents the trivalent or higher valent group; $R_3$ is selected from the group consisting of a hydrogen atom, halogen atom, a saturated or unsaturated aliphatic or cycloaliphatic hydrocarbon residue, an acylamino group and a group —O—$R_6$ or —S—$R_6$ wherein $R_6$ is an aliphatic hydrocarbon residue, and when two or more of $R_3$ groups are present in one molecule, they may be the same or different; $R_4$ and $R_5$ each are selected from the group consisting of an aliphatic hydrocarbon residue, an aryl group, imidazolyl, quinolyl, thienyl, piperazyl, and a hydrogen atom, and $R_4$ and $R_5$ also may be bonded together to form a nitrogen containing hetero ring; n is 1 or 2, m is 2, o is an integer of 1 to 4, p is an integer of 1 to 3, and q is an integer of 1 to 5 with the proviso that when Y or Y' is a divalent aliphatic hydrocarbon or an aromatic hydrocarbon residue, $R'_1$, $R'_2$, $R_1$ and $R_2$ are not cyano or carbamoyl.

2. A process according to claim 1, wherein the color developing agent is an aromatic primary amino compound.

3. A process according to claim 1, wherein the cyan coupler is included in the silver halide emulsion layer of the light-sensitive color photographic material.

4. A process according to claim 1, wherein the cyan coupler is included in the color developer.

5. A process according to claim 1, wherein the radical
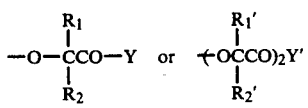
is selected from the group consisting of
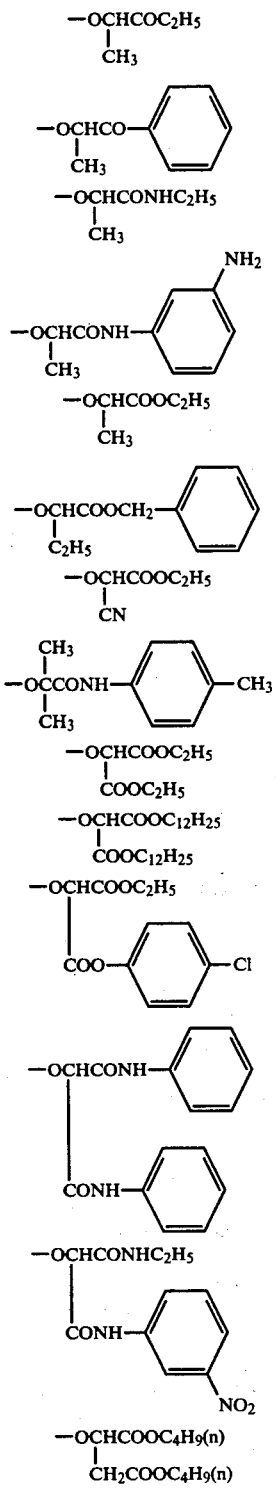
-continued
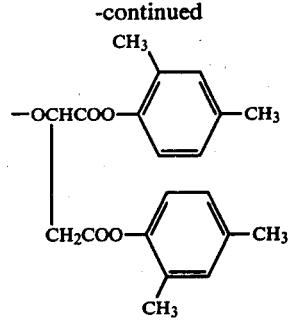
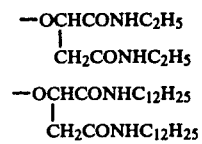
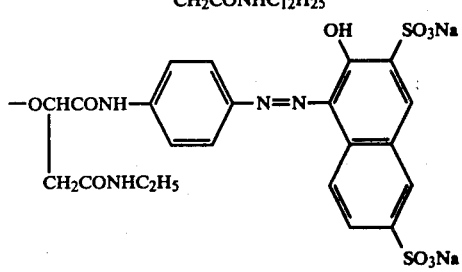
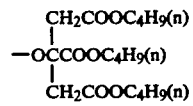
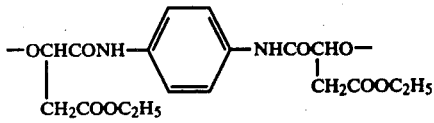
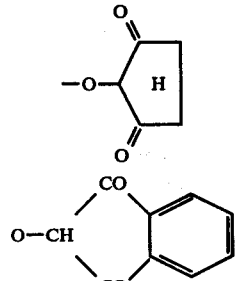
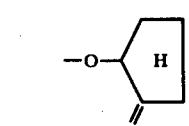
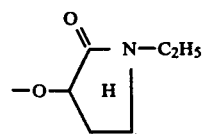
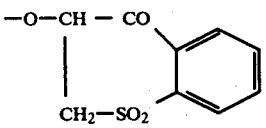
and

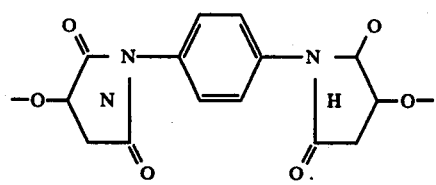

6. A process according to claim 1, wherein the 2-equivalent cyan coupler is selected from the group consisting of

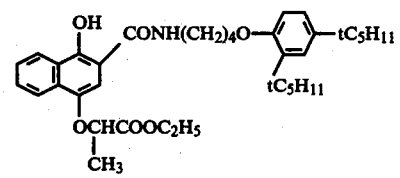

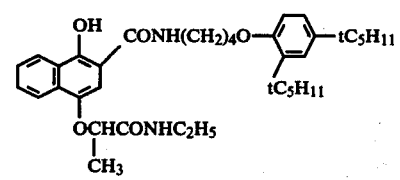

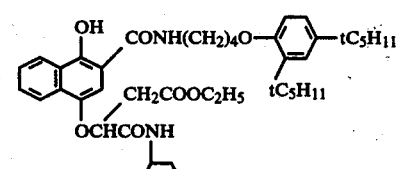

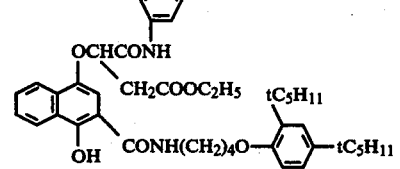

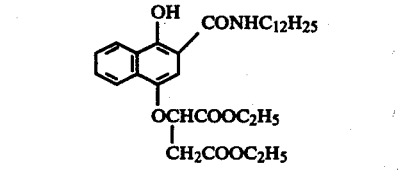

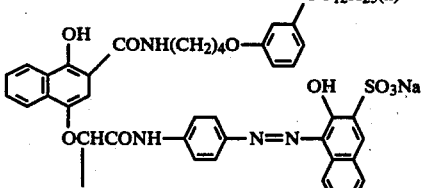

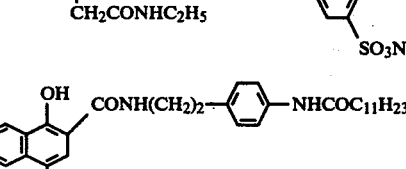

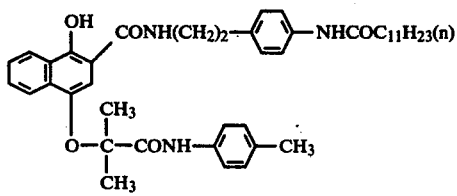

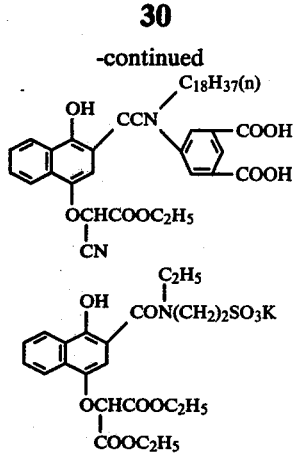

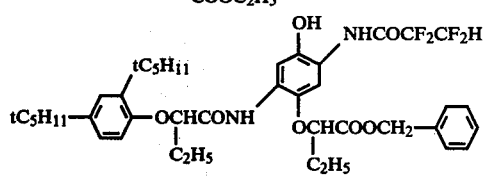

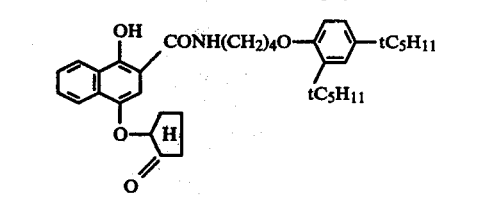

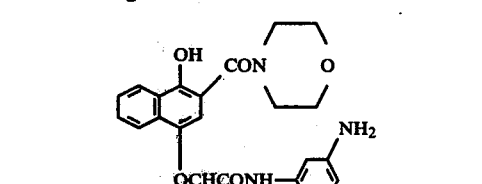

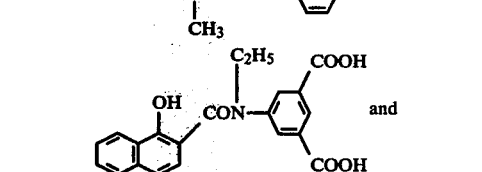

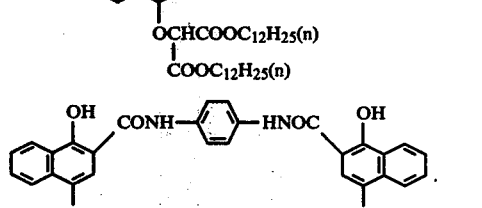

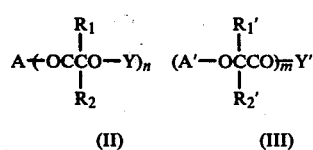

7. A light-sensitive silver halide color photographic material which comprises a support and coated thereon a light-sensitive silver halide emulsion layer containing a photographic 2-equivalent cyan coupler of the following formula (II) or (III):

$$A+OCCO-Y)_n \quad (A'-OCCO)_mY'$$
with $R_1, R_2$ and $R_1', R_2'$ (II)      (III)

wherein A and A' each represent at the active point of the cyan coupler, a cyan coupler residue of the formula

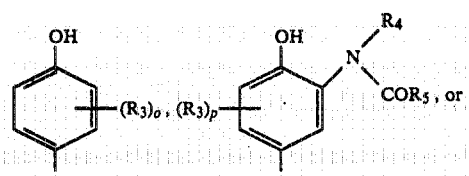

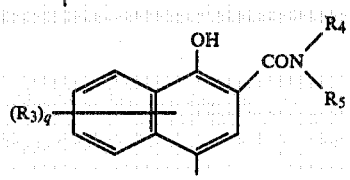

wherein $R_1$, $R_2$, $R_1'$ and $R_2'$ each represent a hydrogen atom, or an organic group selected from the group consisting of nitro, hydroxy, cyano, carboxy, sulfo, thienyl, pyridyl, quinolyl, oxadiazolyl, morpholino, piperazyl, imidazolyl, pyridinylene, quinolylene, monovalent or divalent alkyl, alkenyl, aryl, alkoxy, aryloxy, arylthio, arylazo, acylamino, carbamoyl, carboxylic acid ester, acyl, acyloxy, sulfonamido, sulfamoyl and sulfonyl, with the proviso that at least one $R_1$ and $R_2$ or $R_1'$ and $R_2'$ is an organic group as defined above; Y is selected from the group consisting of monovalent or divalent alkoxy group, phenoxy group, naphthoxy group, aliphatic hydrocarbon amino residue, mercapto group, pyridylene, quinolylene, a divalent aliphatic hydrocarbon, and an aromatic hydrocarbon residue; Y' is selected from the group consisting of a divalent, trivalent or higher valent aliphatic hydrocarbon residue, aromatic hydrocarbon residue, pyridylene, quinolylene, alkylenedioxy group, arylenedioxy group, alkylenediamino residue, arylenediamino residue, and a divalent or trivalent composite group including two or more linked groups selected from the foregoing groups; and $R_1$ and $R_2$ or $R_1'$ or $R_2'$, may be bonded to the carbon atom of the carbonyl group through the group Y or Y' to form a ring, with the proviso that in this instance $R_1$ or $R_2$ and Y represent the divalent group, and $R_1'$ or $R_2'$ represents the divalent group, Y' represents the trivalent or higher valent group; $R_3$ is selected from the group consisting of a hydrogen atom, halogen atom, a saturated or unsaturated aliphatic or cycloaliphatic hydrocarbon residue, an acylamino group and a group —O—$R_6$ or —S—$R_6$ wherein $R_6$ is an aliphatic hydrocarbon residue, and when two or more of $R_3$ groups are present in one molecule, they may be the same or different; $R_4$ and $R_5$ each are selected from the group consisting of an aliphatic hydrocarbon residue, an aryl group, imidazolyl, quinolyl, thienyl, piperazyl, and a hydrogen atom, and $R_4$ and $R_5$ also may be bonded together to form a nitrogen containing hetero ring; n is 1 or 2, m is 2, o is an integer of 1 to 4, p is an integer of 1 to 3, and q is an integer of 1 to 5 with the proviso that when Y or Y' is a divalent aliphatic hydrocarbon or an aromatic hydrocarbon residue, $R'_1$, $R'_2$, $R_1$ and $R_2$ are not cyano or carbamoyl.

8. A color developer for developing exposed light-sensitive silver halide color photographic materials, which comprises p-phenylenediamine and a photographic 2-equivalent cyan coupler of the following formula (II) or (III):

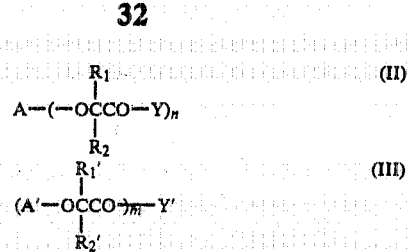

wherein A and A' each represent at the active point of the cyan coupler, a cyan coupler residue of the formula:

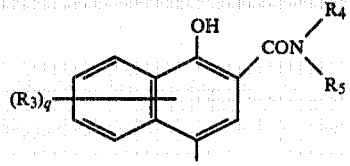

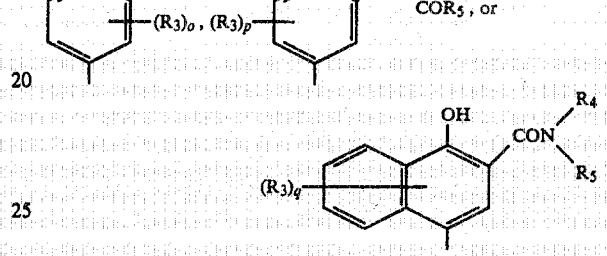

wherein $R_1$, $R_2$, $R_1'$ and $R_2'$ each represent a hydrogen atom, or an organic group selected from the group consisting of nitro, hydroxy, cyano, carboxy, sulfo, thienyl, pyridyl, quinolyl, oxadiazolyl, morpholino, piperazyl, imidazolyl, pyridinylene, quinolylene, monovalent or divalent alkyl, alkenyl, aryl, alkoxy, aryloxy, arylthio, arylazo, acylamino, carbamoyl, carboxylic acid ester, acyl, acyloxy, sulfonamido, sulfamoyl and sulfonyl, with the proviso that at least one $R_1$ and $R_2$ or $R_1'$ and $R_2'$ is an organic group as defined above; Y is selected from the group consisting of monovalent or divalent alkoxy group, phenoxy group, naphthoxy group, aliphatic hydrocarbon amino residue, mercapto group, pyridylene, quinolylene, a divalent aliphatic hydrocarbon, and an aromatic hydrocarbon residue; Y' is selected from the group consisting of a divalent, trivalent or higher valent aliphatic hydrocarbon residue, aromatic hydrocarbon residue, pyridylene, quinolylene, alkylenedioxy group, arylenedioxy group, alkylenediamino residue, arylenediamino residue, and a divalent or trivalent composite group including two or more linked groups selected from the foregoing groups; and $R_1$ and $R_2$ or $R_1'$ or $R_2'$, may be bonded to the carbon atom of the carbonyl group through the group Y or Y' to form a ring, with the proviso that in this instance $R_1$ or $R_2$ and Y represent the divalent group, and $R_1'$ and $R_2'$ represents the divalent group, Y' represents the trivalent or higher valent group; $R_3$ is selected from the group consisting of a hydrogen atom, halogen atom, a saturated or unsaturated aliphatic or cycloaliphatic hydrocarbon residue, an acylamino group and a group —O—$R_6$ or —S—$R_6$ wherein $R_6$ is an aliphatic hydrocarbon residue, and when two or more of $R_3$ groups are present in one molecule, they may be the same or different; $R_4$ and $R_5$ each are selected from the group consisting of an aliphatic hydrocarbon residue, an aryl group, imidazolyl, quinolyl, thienyl, piperazyl, and a hydrogen atom, and $R_4$ and $R_5$ also may be bonded together to form a nitrogen containing hetero ring; n is 1 or 2, m is 2, o is an integer of 1 to 4, p is an integer of 1 to 3, and q is an integer of 1 to 5 with the proviso that when Y or Y' is a divalent aliphatic hydrocarbon or an aromatic hydrocarbon residue, $R'_1$, $R'_2$, $R_1$ and $R_2$ are not cyano or carbamoyl.

* * * * *